United States Patent
Shi et al.

(10) Patent No.: US 9,297,780 B2
(45) Date of Patent: Mar. 29, 2016

(54) HIGH-K METAL GATE DEVICE STRUCTURE FOR HUMAN BLOOD GAS SENSING

(71) Applicant: INTERNATIONAL BUSINESS MACHINES CORPORATION, Armonk, NY (US)

(72) Inventors: Chen Shi, Yorktown Heights, NY (US); Steven E. Steen, Yorktown Heights, NY (US); Yanfeng Wang, Yorktown Heights, NY (US); Sufi Zafar, Yorktown Heights, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 179 days.

(21) Appl. No.: 13/971,446

(22) Filed: Aug. 20, 2013

(65) Prior Publication Data

US 2014/0299922 A1 Oct. 9, 2014

Related U.S. Application Data

(63) Continuation of application No. 13/856,246, filed on Apr. 3, 2013.

(51) Int. Cl.
G01N 27/414 (2006.01)

(52) U.S. Cl.
CPC .................................. *G01N 27/4141* (2013.01)

(58) Field of Classification Search
CPC ............. A61B 5/0002; A61B 5/14532; A61B 2560/0209; A61B 5/6847; A61B 5/002
See application file for complete search history.

(56) References Cited

U.S. PATENT DOCUMENTS

| 6,758,962 | B1 | 7/2004 | Fitzgerald et al. |
| 7,578,974 | B2 | 8/2009 | Izu et al. |
| 8,222,041 | B2 | 7/2012 | Ren et al. |
| 2005/0129573 | A1 | 6/2005 | Gabriel et al. |
| 2005/0247961 | A1 | 11/2005 | Zhou |
| 2007/0227886 | A1* | 10/2007 | Vanaja et al. ............ 204/403.01 |
| 2012/0111093 | A1 | 5/2012 | Brahim et al. |
| 2013/0082337 | A1 | 4/2013 | Chudzik et al. |

(Continued)

FOREIGN PATENT DOCUMENTS

| CN | 102169104 | 8/2011 |
| CN | 102507704 | 6/2012 |
| FR | 2947631 | 1/2011 |

OTHER PUBLICATIONS

English Abstract for Publication No. CN102507704.

(Continued)

*Primary Examiner* — Tony Tran
(74) *Attorney, Agent, or Firm* — F. Chau & Associates, LLC

(57) ABSTRACT

A device structure for detecting partial pressure of oxygen in blood includes a semiconductor substrate including a source region and a drain region. A multi-layer gate structure is formed on the semiconductor substrate. The multi-layer gate structure includes an oxide layer formed over the semiconductor substrate, a high-k layer formed over the oxide layer, a metal gate layer formed over the high-k layer, and a polysilicon layer formed over the metal gate layer. A receiving area holds a blood sample in contact with the multi-layer gate structure. The high-k layer is exposed to contact the blood sample in the receiving area.

19 Claims, 4 Drawing Sheets

(56) References Cited

U.S. PATENT DOCUMENTS

2013/0157432 A1* 6/2013 Beyer et al. .................. 438/299
2014/0256109 A1* 9/2014 Yin et al. ..................... 438/300

OTHER PUBLICATIONS

English Abstract for Publication No. CN102169104.
English Abstract for Publication No. FR2947631.

* cited by examiner

HIGH-K METAL GATE DEVICE STRUCTURE FOR HUMAN BLOOD GAS SENSING

CROSS-REFERENCE TO RELATED APPLICATIONS

This Application is a Continuation of U.S. patent application Ser. No. 13/856,246, filed on Apr. 3, 2013, the entire content of which is herein incorporated by reference.

BACKGROUND

1. Technical Field

The present disclosure relates to human blood gas sensing and, more specifically, to a device structure for human blood gas sensing having a high-k metal gate.

2. Discussion of Related Art

Partial pressure of oxygen in the blood ($pO_2$) is an essential parameter in evaluating the oxygenation status of patients. Effectively measuring $pO_2$ may provide insight into how efficiently the patient's lungs are delivering oxygen into the blood. For this reason, $pO_2$ is carefully monitored for patients in critical condition, such as those in a hospital intensive care unit (ICU), neonatal intensive care unit (NICU), emergency room/department, etc, Traditional $pO_2$ sensors make use of the Clark principal, which utilized electrochemical oxygen analyzers that measure electrochemical reduction of oxygen by measuring oxygen tension amperometrically at a negatively polarized electrode, known as the "Clark" electrode.

These existing approaches for $pO_2$ sensing may be sensitive to storage conditions such as temperature and humidity, may have a short shelf time, and may have a relatively high cost associated with their use owing to the expensive analysis machines that are generally used.

BRIEF SUMMARY

A device structure for detecting partial pressure of oxygen in blood includes a semiconductor substrate including a source region and a drain region. A multi-layer gate structure is formed on the semiconductor substrate. The multi-layer gate structure includes an oxide layer formed over the semiconductor substrate, a high-k layer formed over the oxide layer, a metal gate layer formed over the high-k layer, and a polysilicon layer formed over the metal gate layer. A receiving area holds a blood sample in contact with the multi-layer gate structure. The high-k layer is exposed to contact the blood sample in the receiving area.

Conductive connectors may be formed over the source and drain regions of the semiconductor substrate for applying a voltage to the source and drain regions of the semiconductor substrate therethrough and to measure a current shift resulting from the presence of the blood sample in the receiving area.

Gate terminals may be formed on the multi-layer gate structure for driving a current through the metal gate layer to provide annealing to the blood sample in the receiving area.

The multi-layer gate structure may be a common gate structure formed over a plurality of semiconductor substrates that are each similar or identical to the semiconductor substrate. The common gate structure may have a comb structure on at least one end thereof for increasing a contact area between the high-k layer and the blood sample in the receiving area.

The semiconductor substrate may further include a conducting channel between the source and drain regions, the multi-layer gate structure formed over the conducting channel. The source region, the drain region, and the conducting channel may be formed from a N/P/N field effect transistor formed in the semiconductor substrate.

The oxide layer may include silicon dioxide. The oxide layer may be substantially 0.05 µm thick. The high-k layer may include hafnium(IV) oxide ($HfO_2$). The high-k layer may be substantially 0.05 µm thick.

The metal gate layer may include titanium nitride (TiN). The metal gate layer may be substantially 0.1 µm thick.

A plurality of conductive connectors may be formed over the silicon substrate, on opposite sides of the multi-layer gate structure, and they may make contact with the source and drain regions, respectively. Each of the plurality of conductive connectors may include tungsten. Each of the plurality of conductive connectors may be substantially 0.5 µm thick. Each of the plurality of conductive connectors may be formed over a respective nickel silicon (Nisi) contact formed in the semiconductor substrate.

Opposite sides of the multi-layer gate structure may each be spaced apart from a nearest conductive connector of the plurality of conductive connectors by substantially 0.5 µm. The multi-layer gate structure may be substantially 1 µm wide.

A porous membrane layer may be formed over the multi-layer gate structure. The porous membrane layer may include a plurality of pores, each of which is substantially 1 µm wide.

A method for fabricating a device structure for detecting partial pressure of oxygen in blood includes forming a multi-layer gate structure on a semiconductor substrate by forming an oxide layer over the semiconductor substrate, forming a high-k layer formed over the oxide layer, forming a metal gate layer formed over the high-k layer, and forming a polysilicon layer formed over the metal gate layer. A spacer may be formed on opposite sides of the multi-layer gate structure. A source region and a drain region may be formed within the silicon substrate by implanting impurities therein after the spacer has been formed. The spacer is removed after the source and drain regions have been formed.

Conductive connectors may be formed over the source and drain regions of the semiconductor substrate for applying a voltage to the source and drain regions of the semiconductor substrate therethrough and to measure a current shift resulting from the presence of the blood sample in the receiving area.

Gate terminals may be formed on the multi-layer gate structure for driving a current through the metal gate layer to provide annealing to the blood sample in the receiving area.

The multi-layer gate structure may be a common gate structure formed over a plurality of semiconductor substrates that are each similar or identical to the semiconductor substrate. The common gate structure may have a comb structure on at least one end thereof for increasing a contact area between the high-k layer and the blood sample in the receiving area.

The semiconductor substrate may further include a conducting channel between the source and drain regions, the multi-layer gate structure formed over the conducting channel. The source region, the drain region, and the conducting channel may be formed from a N/P/N field effect transistor formed in the semiconductor substrate.

The oxide layer may be formed comprising silicon dioxide. The oxide layer may be formed with a thickness of substantially 0.05 µm.

The high-k layer may be formed comprising hafnium(IV) oxide ($HfO_2$). The high-k layer may be formed with a thickness of substantially 0.05 µm.

The metal gate layer may be formed comprising titanium nitride (TiN). The metal gate layer may be formed with a thickness of substantially 0.1 μm.

A plurality of conductive connectors may be formed over the silicon substrate, on opposite sides of the multi-layer gate structure, making contact with the source and drain regions, respectively. Each of the plurality of conductive connectors may be formed including tungsten.

Each of the plurality of conductive connectors may be formed having a thickness of substantially 0.5 μm.

Each of the plurality of conductive connectors may be formed over a respective nickel silicon (NiSi) contact formed in the semiconductor substrate.

Opposite sides of the multi-layer gate structure are each formed to be spaced apart from a nearest conductive connector of the plurality of conductive connectors by substantially 0.5 μm.

The multi-layer gate structure may be formed having a width of substantially 1 μm. A porous membrane layer may be formed over the multi-layer gate structure. The multi-layer gate structure may be formed using deposition, lithography, or reactive-ion etching (RIE). The spacer may be formed using deposition or reactive-ion etching (RIE).

The spacer may be removed using reactive-ion etching (RIE). The source and drain regions and the metal gate layer may each be formed using lithography, deposition, or annealing.

A method for testing partial pressure of oxygen within blood includes applying a blood sample to make contact with a multi-layer gate structure formed on a semiconductor substrate. The multi-layer gate structure includes an oxide layer formed over the semiconductor substrate, a high-k layer formed over the oxide layer, a metal gate layer formed over the high-k layer, and a polysilicon layer formed over the metal gate layer. A current is sent though the metal gate later to obtain a desired temperature within the multi-layer gate structure. A first voltage is applied to the source, a second voltage to the drain and a third voltage to the multi-layer gate structure to create a current therethrough. A shift in the current is measured through the multi-layer gate structure. A partial pressure of oxygen in the blood sample is determined based on the measured current shift.

The first and second voltages may be applied to the source and drain via conductive connectors formed thereon. The multi-layer gate structure may be a common gate structure formed over a plurality of semiconductor substrates that are each similar or identical to the semiconductor substrate. The common gate structure may have a comb structure on at least one end thereof for increasing a contact area between the high-k layer and the blood sample applied to the multi-layer gate structure.

BRIEF DESCRIPTION OF THE SEVERAL VIEWS OF THE DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION

Figure 1:
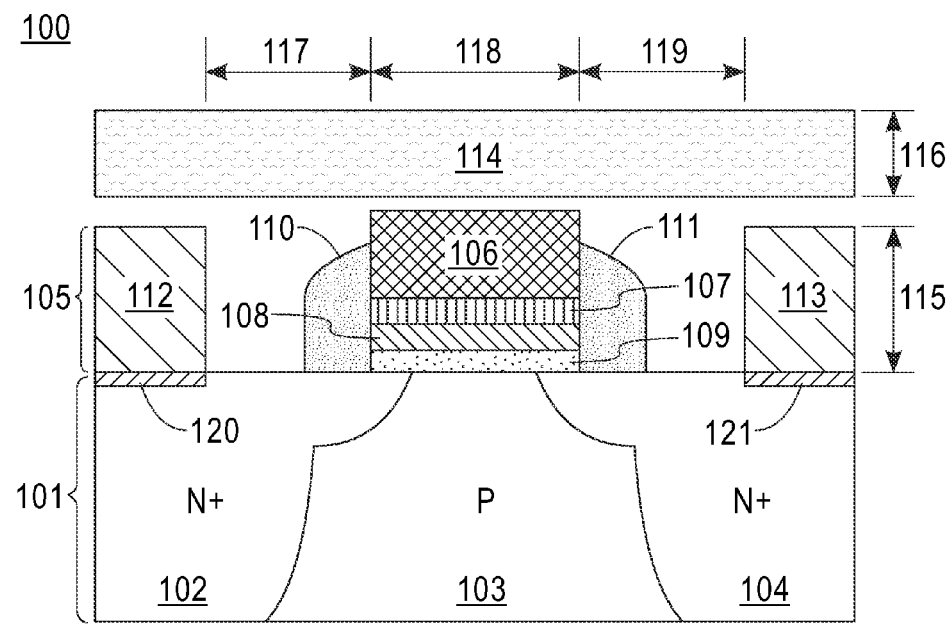
FIG. 1 is a diagram illustrating a structure of a high-k metal gate FET for sensing $pO_2$ in accordance with exemplary embodiments of the present invention.

In describing exemplary embodiments of the present disclosure illustrated in the drawings, specific terminology is employed for sake of clarity. However, the present disclosure is not intended to be limited to the specific terminology so selected, and it is to be understood that each specific element includes all technical equivalents which operate in a similar manner.

Exemplary embodiments of the present invention provide a device and approach for measuring partial pressure of oxygen in the blood ($pO_2$) that may be less sensitive to storage conditions, may have a longer shelf time, and may be implemented at a lower cost than conventional approaches. Additionally, exemplary embodiments of the present invention may be made small enough for portable and/or home use and may be integrated into existing biosensor chip devices such as the EPOC BGEM blood gas and electrolyte card provided by ALERE.

Exemplary embodiments of the present invention relate to the fabrication and use of a field effect transistor (FET) having a gate structure including a high-k material such as Hafnium Oxide ($HfO_2$) which may be very sensitive to oxygen concentration. The high-k metal gate FET may also have a spacer removed to expose a perimeter of the gate oxide for stronger sensitivity. The $pO_2$ sensing device may include multiple high-k metal gate FETs. A blood sample may be dropped on or made to flow through patterned array elements to bring the sample to an anneal temperature to shift the temperature-sensitive flatband voltage (Vfb) and to drive current for sensing oxygen partial pressure.

Figure 2:
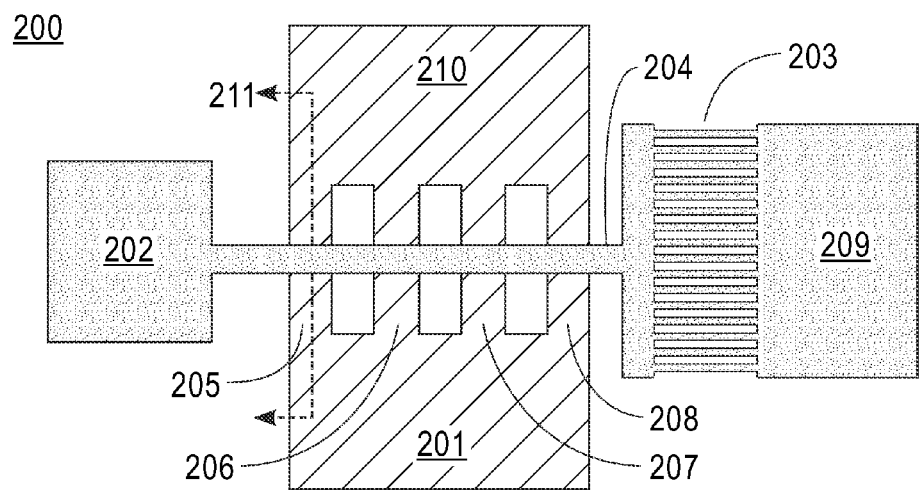
FIG. 2 is a planar view of a $pO_2$ sensing device utilizing the high-k metal gate FET of FIG. 1 in accordance with exemplary embodiments of the present invention.
Figure 3A:
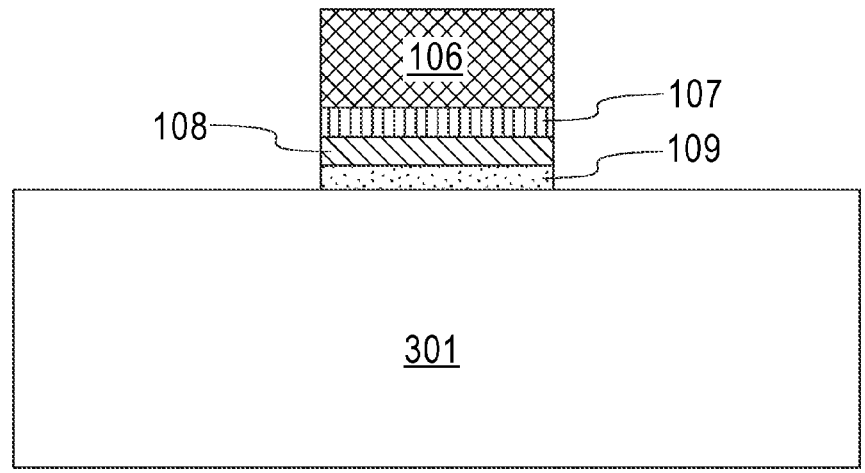
FIGS. 3A-3D are schematic diagrams illustrating stages in an approach for fabricating a $pO_2$ sensing device in accordance with exemplary embodiments of the present invention.
Figure 3B:
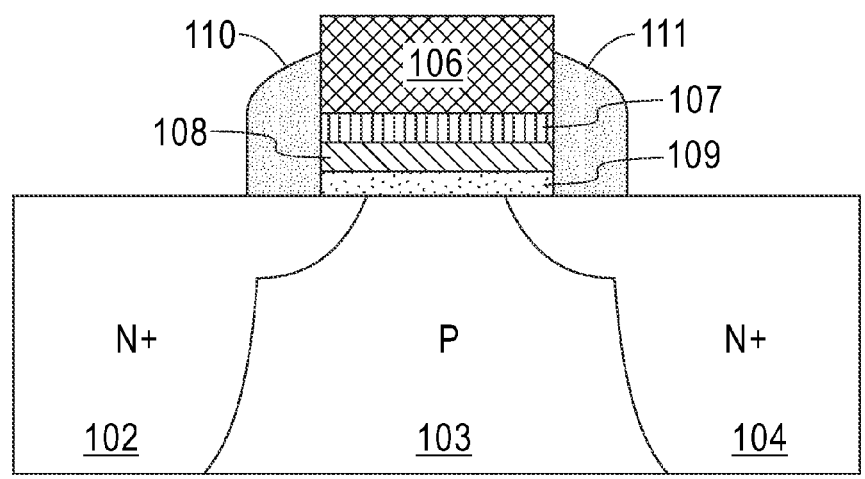
Figure 3C:
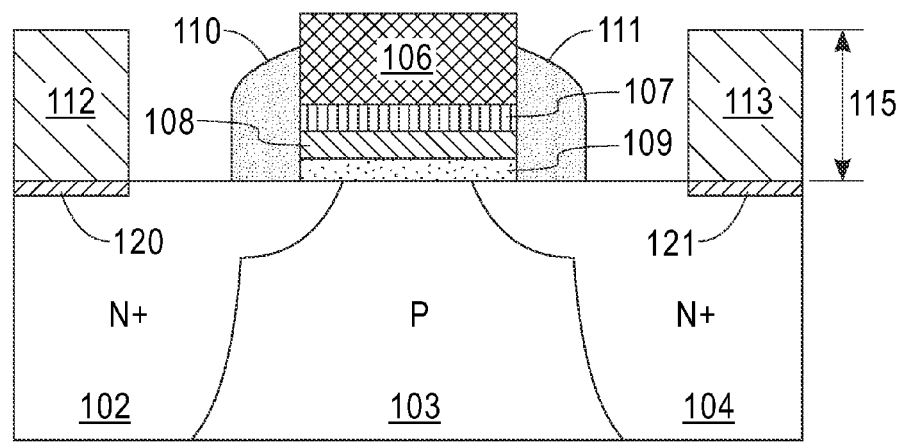
Figure 3D:
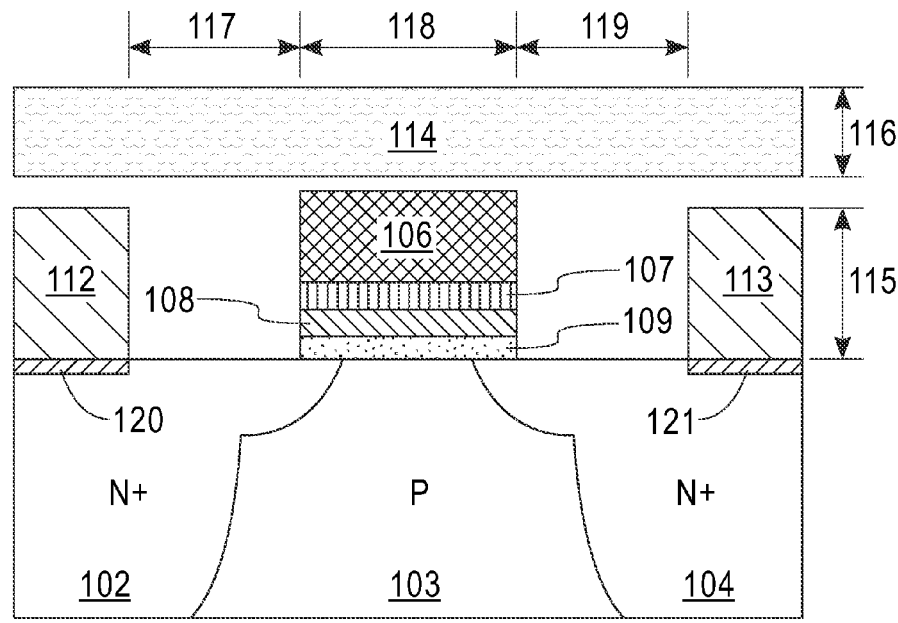

FIG. 1 is a diagram illustrating a structure of a high-k metal gate FET for sensing $pO_2$ in accordance with exemplary embodiments of the present invention. FIG. 2 is a planar view of a $pO_2$ sensing device utilizing the high-k metal gate FET of FIG. 1 in accordance with exemplary embodiments of the present invention.

In FIG. 1, the FET 100 includes a substrate 101 made of silicon or some other semiconductor substance. Within the silicon substrate, there may be a p-type doped region 103 and two n-type doped regions 102 and 104. The two n-type doped regions 102 and 104 form source and drain respectively. A center region 105 is formed over the substrate 101. The center region includes a gate stack made of multiple layers 106-109 and conductive connectors 112 and 113 that make electrical contact with the source 102 and drain 104, respectively. Silicon dioxide ($SiO_2$) spacers 110 and 111 may abut the gate stack layers 106-109. These spacers may be removed during fabrication to enhance the oxygen sensitivity of the gate, as discussed in detail below.

The multi-layer gate stack may include a silicon dioxide ($SiO_2$) layer 109 over the substrate 101. The $SiO_2$ layer 109 may be, for example, approximately 0.05 μm thick. Above the $SiO_2$ layer 109 may be a high-k layer 108. The high-k layer may include, for example, hafnium(IV) oxide ($HfO_2$). The high-k layer 108 may be, for example, approximately 0.05 μm thick. The high-k layer 108 may include a material that has a dielectric constant greater than that of silicon dioxide.

Thereabove may be a metal gate layer (107), which may include, for example titanium nitride (TiN), may be formed. The metal gate layer (107) may be, for example, approximately 0.1 μm thick. On top of the metal gate later (107) a polysilicon layer (106) may be formed.

The conductive connectors 112 and 113 may be made of a conductive material such as tungsten. The conductive connectors 112 and 113 have thicknesses 115, that may be, for example, approximately 0.5 μm. Under the conductive connectors 112 and 113, and located within the substrate 101 may be nickel silicon (NiSi) contacts 120 and 121. The NiSi contacts may facilitate electrical connection to the source and drain 102 and 104, respectively, and may be formed, for example, by annealing Nickel on top of the silicon substrate 101.

The gate stack, and in particular, the polysilicon layer 106, may be spaced apart from the conductive connectors 112 and 113 by distances 117 and 119, which may be, for example, approximately 0.5 μm. The width of the gate stack, and in particular, the polysilicon layer 106 is width 118 and this width may be, for example, approximately 1 μm.

Above the gate stack, and in particular, the polysilicon layer 106, may be a filter 114. The filter may include a set of pores for allowing blood to flow therethrough while filtering the blood cells and platelets as well as any other unwanted substances. The filter layer may have pores of a size of, for example, 1 μm.

In operation, oxygen from the blood may fill the vacancy states of the high-k layer 108 and this may cause a shift in the flatband voltage with respect to temperature (Vt). The degree of the shift in Vt may be influenced by the partial pressure of oxygen. As the diffusion of oxygen may stabilize within seconds, the Vt shift may be determined by monitoring the current across the source and drain 102 and 104 before and after the diffusion of the oxygen from the blood sample, given a constant gate/drain voltage.

In the top-down planar view of FIG. 2, the $pO_2$ sensing device 200 is shown to include four FETs 100 (205, 206, 207, and 208). The gates of each FET are connected by a common gate stack 204 which makes electrical contact with a contact pad 202 on one side and a comb structure 203 on an opposite side. The comb structure 203 is connected to a contact pad 209. The hatched line 211 shows the cross section of the FET illustrated in FIG. 1. The comb structure 203 may be used to enhance oxygen sensitivity by increasing the area of contact between the high-k layer 108 of the common gate stack 204, as the gate stack including layers 106-109 extends throughout the entire common gate stack 204 as well as the comb structure.

As the flatband voltage is temperature sensitive, the $pO_2$ sensing device 200 may provide for thermal annealing so that the temperature may be accurately controlled. Exemplary embodiments of the present invention may provide for in-situ thermal annealing by applying voltage through two gate terminals to result in local self-heating. Application of the voltage to result in local self-heating may be performed, for example, by applying a high current through the metal gate layer 107 through contacts disposed on the gate layer. As discussed above, the metal gate layer, which may include TiN, may have a thermal conductivity of approximately 40 W/(mk), a thermal resistance of approximately $6.25 \times 10^4$, assuming a TiN layer 0.4 μm wide, 0.04 μm thick and 0.04 μm long. Accordingly, the high current for providing heating may be on the order of $1 \times 10^{-2}$ W if applying 1V across the TiN layer. Under such a current, the temperature increase may be as high as approximately 625K.

Exemplary embodiments of the present invention may utilize a two-step approach for detecting $pO_2$ using the $pO_2$ sensing device described above. First, a voltage may be applied on the gate terminals to perform annealing so that a desired temperature may be obtained. Then, voltage may be applied on the gate, source, and drain to measure current shift for sensing $pO_2$. The $pO_2$ may be calculated from the current shift before and after the diffusion of oxygen from the blood into the high-k layer as the current shifts caused by various oxygen levels may be known for the given temperature.

Figure 4:
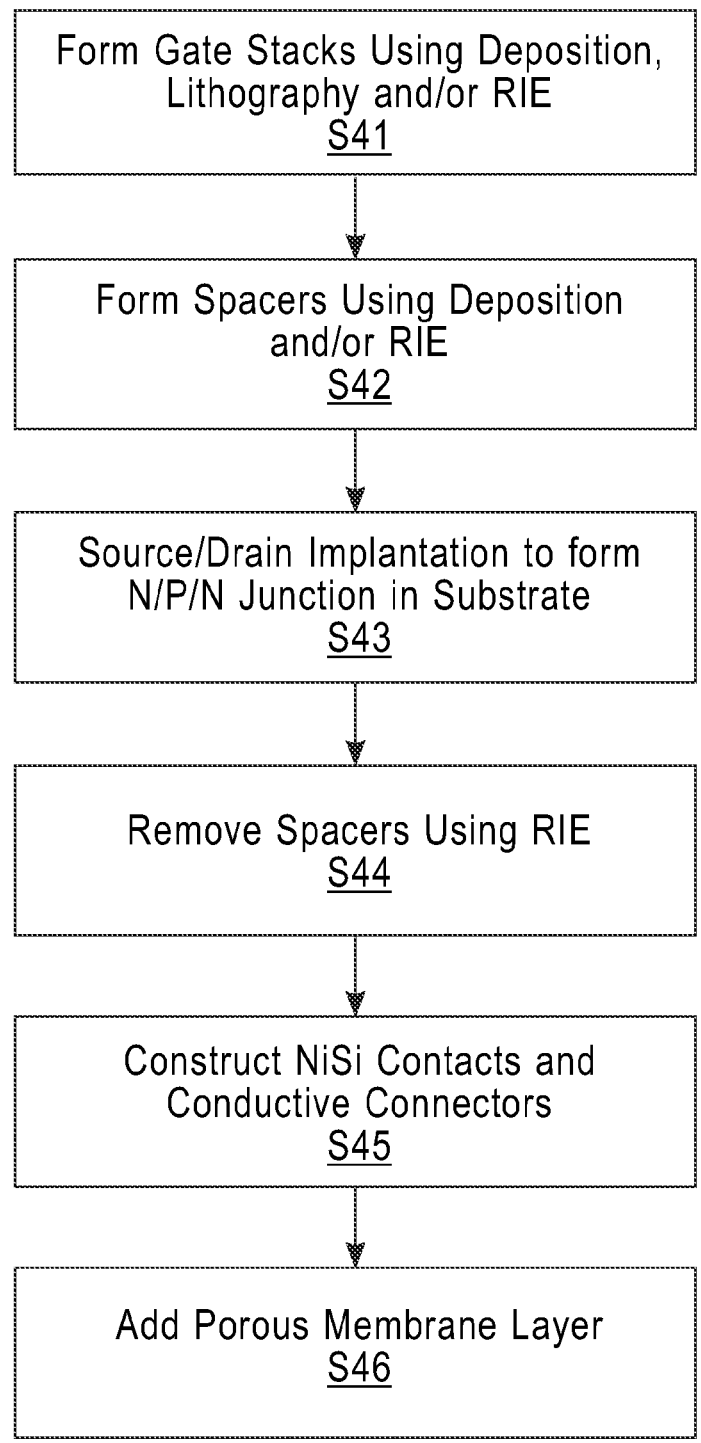
FIG. 4. is a flow chart illustrating method steps for fabricating a $pO_2$ sensing device in accordance with exemplary embodiments of the present invention.

FIGS. 3A-3D are schematic diagrams illustrating an approach for fabricating a $pO_2$ sensing device in accordance with exemplary embodiments of the present invention. FIG. 4 is a flow chart illustrating method steps for the fabricating approach of FIGS. 3A-3D. As may be seen in FIG. 3A, first, deposition, lithography, and/or reactive-ion etching (RIE) may be used to successively form the gate stacks 109, 108, 107, and 106 over the silicon substrate 301 (Step S41). Then, as may be seen in FIG. 3B, spacers 110 and 111, may be formed using deposition and/or PIE (Step S42). Source and drain implantation may then be performed to form N/P/N junctions (Step S43). The spacers may help to define the N/P/N regions during this doping step. Then, as may be seen in FIG. 3C, the spacers may be removed, for example, by RIE (Step S44). Lithography, deposition, and/or annealing steps may then be performed to construct the nickel silicon (NiSi) contacts 120 and 121 and the conductive connectors 112 and 113 (Step S45). Thereafter, as may be seen in FIG. 3D, a porous membrane layer 114 is added (Step S46). as a filter so that unwanted substances may be filtered from the blood prior to making contact with the high-k layer 108 of the $pO_2$ sensing device.

Exemplary embodiments described herein are illustrative, and many variations can be introduced without departing from the spirit of the disclosure or from the scope of the appended claims. For example, elements and/or features of different exemplary embodiments may be combined with each other and/or substituted for each other within the scope of this disclosure and appended claims.

What is claimed is:

1. A device structure for detecting partial pressure of oxygen in blood, comprising:
    a semiconductor substrate including a source region and a drain region;
    a multi-layer gate structure formed on the semiconductor substrate, the multi-layer gate structure comprising:
    an oxide layer formed over the semiconductor substrate;
    a high-k layer formed over the oxide layer;
    a metal gate layer formed over the high-k layer; and
    a polysilicon layer formed over the metal gate layer;
    a porous membrane layer formed over an entirety of the multi-layer gate structure;
    a receiving area for holding a blood sample in contact with a cross-section of the multi-layer gate structure such that the blood sample is filtered through the porous membrane prior to making contact with the cross-section of the multi-gate structure and such that the high-k layer is exposed to contact the blood sample in the receiving area;
    a processor for calculating a partial pressure of oxygen in the blood sample based on a detected shift in a flatband voltage of the multi-layer gate structure with respect to temperature; and
    wherein the porous membrane layer is configured to pass oxygenated blood therethrough such that the oxygenated blood makes contact with high-k layer and oxygen of the oxygenated blood fills vacancies within the high-k layer to shift the flatband voltage while platelets are prevented from making contact with the high-k layer.

2. The device structure of claim 1, wherein conductive connectors are formed over the source and drain regions of the semiconductor substrate for applying a voltage to the source and drain regions of the semiconductor substrate therethrough and to measure a current shift resulting from the presence of the blood sample in the receiving area, the measured current shift being used to detect the shift in the flatband voltage.

3. The device structure of claim 1, additionally including gate terminals formed on the multi-layer gate structure for driving a current through the metal gate layer to provide annealing to the blood sample in the receiving area.

4. The device structure of claim 1, wherein the multi-layer gate structure is a common gate structure formed over a plurality of semiconductor substrates that are each similar or identical to the semiconductor substrate, wherein the common gate structure has a comb structure on at least one end thereof for increasing a contact area between the high-k layer and the blood sample in the receiving area.

5. The device structure of claim 1, wherein the semiconductor substrate further includes a conducting channel between the source and drain regions, the multi-layer gate structure formed over the conducting channel.

6. The device structure of claim 5, wherein the source region, the drain region, and the conducting channel are formed from a N/P/N field effect transistor formed in the semiconductor substrate.

7. The device structure of claim 1, wherein the oxide layer comprises silicon dioxide.

8. The device structure of claim 1, wherein the oxide layer is substantially 0.05 µm thick.

9. The device structure of claim 1, wherein the high-k layer comprises hafnium(IV) oxide ($HfO_2$).

10. The device structure of claim 1, wherein the high-k layer is substantially 0.05 µm thick.

11. The device structure of claim 1, wherein the metal gate layer comprises titanium nitride (TiN).

12. The device structure of claim 1, wherein the metal gate layer is substantially 0.1 µm thick.

13. The device structure of claim 1, further comprising a plurality of conductive connectors formed over the silicon substrate, on opposite sides of the multi-layer gate structure, and making contact with the source and drain regions, respectively.

14. The device structure of claim 13, wherein each of the plurality of conductive connectors comprises tungsten.

15. The device structure of claim 13, wherein each of the plurality of conductive connectors is substantially 0.5 µm thick.

16. The device structure of claim 13, wherein each of the plurality of conductive connectors is formed over a respective nickel silicon (Nisi) contact formed in the semiconductor substrate.

17. The device structure of claim 1, wherein opposite sides of the multi-layer gate structure are each spaced apart from a nearest conductive connector of the plurality of conductive connectors by substantially 0.5 µm.

18. The device structure of claim 1, wherein the multi-layer gate structure is substantially 1 µm wide.

19. The device structure of claim 1, wherein the porous membrane layer comprises a plurality of pores, each of which is substantially 1 µm wide.

* * * * *